United States Patent [19]

Marinkovich

[11] Patent Number: 4,459,360
[45] Date of Patent: Jul. 10, 1984

[54] MULTIPLE-COMPONENT BINDING ASSAY SYSTEM AND METHOD OF MAKING AND USING IT

[75] Inventor: Vincent A. Marinkovich, Palo Alto, Calif.

[73] Assignee: Mast Medical Industries, Ltd., Mountain View, Calif.

[21] Appl. No.: 308,935

[22] Filed: Oct. 5, 1981

[51] Int. Cl.³ .................... G01N 33/58; G01N 33/60; G01N 23/06; B65D 71/00
[52] U.S. Cl. .................................... 436/513; 422/61; 422/68; 422/71; 436/530; 436/804; 436/808; 436/810
[58] Field of Search ................. 424/1, 12; 422/56–58, 422/61, 68; 436/530, 513, 804, 808, 810

[56] References Cited

U.S. PATENT DOCUMENTS

| | | |
|---|---|---|
| 2,190,745 | 2/1940 | Vollmer . |
| 2,278,339 | 3/1942 | Vollmer . |
| 3,556,080 | 1/1971 | Heim . |
| 3,802,782 | 4/1974 | Natelson ............................ 23/259 |
| 3,852,035 | 12/1974 | Wood et al. ......................... 23/259 |
| 3,941,876 | 3/1976 | Marinkovich . |
| 4,031,197 | 6/1977 | Marinkovich . |
| 4,034,601 | 7/1977 | Geiger ............................ 23/230 B |
| 4,180,383 | 12/1979 | Johnson . |
| 4,205,689 | 6/1980 | Brennan . |
| 4,219,530 | 8/1980 | Kopp et al. ........................... 422/69 |
| 4,270,548 | 6/1981 | Brennan . |
| 4,276,259 | 6/1981 | Eibl et al. ............................ 424/1 |
| 4,327,073 | 4/1982 | Huang .................................. 424/1 |
| 4,331,650 | 5/1982 | Brewer et al. ....................... 422/56 |

Primary Examiner—Christine M. Nucker
Attorney, Agent, or Firm—Fulwider, Patton, Rieber, Lee & Utecht

[57] ABSTRACT

A multiple component binding assay system, and related methods of making and using it, having a plurality of coated filaments mounted at their opposite ends on a support, in a predetermined spaced relationship, for simultaneously screening a liquid test sample for a plurality of components. The system is particularly suitable for screening the sample for IgE class antibodies specific for certain allergens. The filaments are preferably cotton threads, each thread binding a different allergen through a covalent bond. The support, which is preferably cut away adjacent the mid-portion of each filament to reduce background interference, is composed of a plastic or other water insoluble material, permitting inexpensive and relatively simple manufacture. After any IgE class antibodies present in the liquid sample have reacted with the corresponding allergens coated on the filaments, they are detected using second antibodies labeled with radioactive, fluorescent or enzymatic tracers. By using a high energy radioactive tracer, such as $^{125}I$, autoradiographic techniques with phosphor screen enhancement allow for diagnostic analysis by a densitometer or even the unaided human eye.

57 Claims, 7 Drawing Figures

MULTIPLE-COMPONENT BINDING ASSAY SYSTEM AND METHOD OF MAKING AND USING IT

BACKGROUND OF THE INVENTION

This invention relates to binding assays for use in diagnostic analysis of liquid specimens and, more particularly, to a diagnostic system capable of detecting the presence of IgE class antibodies for allergy screening.

One characteristic of mammals and other highly developed animals is the ability to protect themselves against the veritable onslaught of invading organisms and foreign material encountered on a constant or periodic basis. The protection originates in the initiation by the organism or foreign material of an immunogenic response in the animal. An important aspect of this immunogenic response is the production of immunoglobulins, so-called antibodies, against antigenic sites on the organisms or foreign material.

For reasons not yet completely understood, certain antigenic materials, known as allergens, often induce a hypersensitive response in human beings. This hypersensitivity, or allergy, can manifest itself in a number of readily identifiable symptoms, notably, hay fever, asthma, eczema, hives and localized swelling.

Traditionally, diagnostic analysis for the presence of this hypersensitivity in patients was accomplished with skin tests or provocation tests. In provocation tests the patient inhales the suspected allergen in aerosol form, whereas skin tests require applying the allergen to the patient's skin. Both tests necessitate monitoring the patient for evidence of allergic symptoms and require significant amounts of trained personnel time for proper evaluation. Moreover, in some cases exposure to the allergen can induce a strong allergic response, resulting in unnecessary discomfort, or even harm, to the patient.

As a result of discovery that a class of immunoglobulins, specifically IgE class antibodies, were in large part responsible for the allergic response, diagnosticians developed in vitro tests for IgE class antibodies utilizing standard radioimmunoassay techniques on serum. By way of example, several types of such tests can be found in U.S. Pat. Nos. 3,877,307 and 4,243,651.

Successful research was also accomplished with respect to techniques for the screening of different IgE class antibodies, and by way of example, such techniques can be found in U.S. Pat. Nos. 3,941,876 and 4,031,197. Basically, the techniques described in these patents include coating an elongated cellulosic body (e.g., a strip of paper) with separate identified allergens to form bands or islands, which are separated from one another by allergen-free areas. When this elongated body of cellulose material coated with the allergens is contacted with a test serum, serum IgE class antibodies specific for the coated allergens will attach to the appropriate places. After washing the cellulosic body and subsequently incubating it with labeled antibodies that are reactive with the attached IgE class antibodies, the bands and islands are analyzed for the presence of labeled antibodies. The information gleaned from the analysis provides an indication of the patient's allergic tendencies.

The methods and apparatus described in connection with the aforementioned screening patents are acceptable. However, the manufacture of the bands and islands on the cellulosic material is somewhat arduous and time consuming, typically requiring use of a jig for proper allergen coating. Also, for best results, all of the allergens should be coated on the cellulosic material at one time, mandating simultaneous allergen preparation. These constraints encumber the manufacturing process and limit the flexibility of the screening.

Accordingly, those concerned with the development and use of immunoassay techniques and related apparatus have recognized the desirability for further improvement in allergy screening systems. In particular, there has been a desire for improved and more economical manufacturing methods of devices useful for such screening. The present invention fulfills these needs.

SUMMARY OF THE INVENTION

The present invention provides a diagnostic system for use in the analysis of liquid specimens through binding assays, the system having a plurality of filaments coated with binding assay components from different assays for simultaneous contact with the liquid specimen and coincident measurement of the binding assay components. Moreover, the system construction of the present invention is relatively easy to manufacture, flexible, and inexpensive to make and use.

More specifically, a presently preferred embodiment of the invention is a diagnostic kit which includes a support having a plurality of cotton threads supported in a predetermined spaced relation for simultaneous contact with a liquid test sample. At least two of the threads are coated with allergen compositions specific to different IgE class antibodies for screening purposes. The threads are preferably made from cotton, a high molecular weight polysaccharide, so that the allergen can be covalently bound through cyanogen halide induced linkages. The preferred kit further includes second antibodies (antibodies reactive with the IgE class antibodies) that enable detection of IgE class antibodies bound to the threads. The second antibodies are preferably labeled with a radioactive tracer, such as $^{125}I$, but may also be labeled with a fluorescent tracer, enzyme, enzyme substrate or coenzyme.

Another aspect of the invention is a method of detecting the presence of biological agents in a liquid specimen through the use of binding assays. This method includes the steps of incubating a liquid specimen with a plurality of filaments supported in a predetermined spaced relationship, at least two of the filaments being coated with a binding assay component from different assays; and analyzing the filaments to coincidentally determine the amount of multiple biological agents interacting with the binding assay components coated on the filament. The binding assay is preferably an immunoassay, and the analysis accomplished by autoradiography.

When screening for the presence of multiple allergen-specific IgE class antibodies in a liquid sample, the method includes the steps of: incubating the test sample with a plurality of filaments supported in a predetermined spaced relationship and coated with allergens specific to the IgE class antibodies in question; removing the filaments from the test sample; incubating the filaments with a solution containing labeled second antibodies against the IgE class antibodies; removing the filaments from the solution; and analyzing the filaments to determine the presence of the second antibodies.

If the second antibodies are radioactively labeled, such as with $^{125}I$, the analysis can be accomplished with a gammacounter. An alternative analysis entails placing the filaments proximate to a film for exposure, and then analyzing the film's exposure by the unaided human eye, by a densitometer or by a scanning densitometer. A phosphor screen placed between the film and the filaments, often enhances film exposure.

When the second antibodies are labeled with a fluorescent tracer, the analysis can be accomplished with a fluorometer. Similarly, if the label is an enzyme or enzyme substrate, a spectrophotometer may be utilized.

A further aspect of the invention is a method of making an apparatus useful in the analysis of liquid specimens through binding assays. The method includes the steps of coating a filament with a component of a binding assay; and attaching a plurality of filaments in a spaced relationship to a support. At least two of the filaments are coated with components from different binding assays. When the filaments are made of cotton thread and the support of plastic, the support can be easily sliced into a plurality of elongated strips of a predetermined size. Further, the support can be partially cut away behind the filaments to reduce the background interference.

More specifically, a method of making a miniature apparatus for use in the simultaneous determination of the presence of multiple allergen-specific IgE class antibodies in a liquid test sample is provided. The method includes the steps of coating a filament with an allergen composition specific to at least one of said IgE class antibodies; and attaching a plurality of these filaments to a support. At least two of the filaments attached to the support are coated with different allergen compositions. Again, the support can readily be sliced into a plurality of elongated strips of a predetermined size. The allergen composition can be composed of a mixture of related allergens, such as grass mix, mugwort mix, olive mix, ragweed mix, walnut mix, alternaria mix, dematiaceae mix or pennicillium mix. Furthermore, the allergen composition can be composed of a defatted and extracted allergen.

It will be appreciated from the foregoing that the present invention represents a significant advance over previously available screening systems for allergy detection, principally because its manufacture is so simple and economical. Other aspects and advantages of the invention will become apparent from the following more detailed description taken in conjunction with the accompanying drawings.

DESCRIPTION OF THE PREFERRED EMBODIMENT

Figure 1:
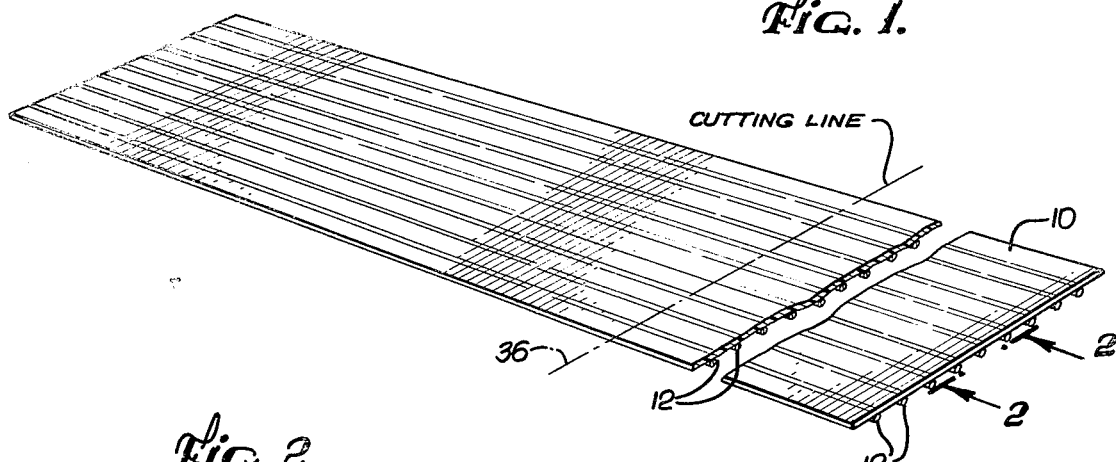
FIG. 1 is a perspective view of a system embodying the invention and showing a plurality of threads attached to an elongated support during manufacture.
Figure 2:
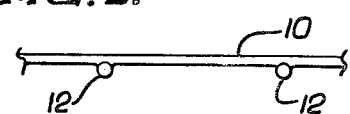
FIG. 2 is an enlarged, fragmentary end view taken substantially along line 2—2 of FIG. 1.
Figure 3:
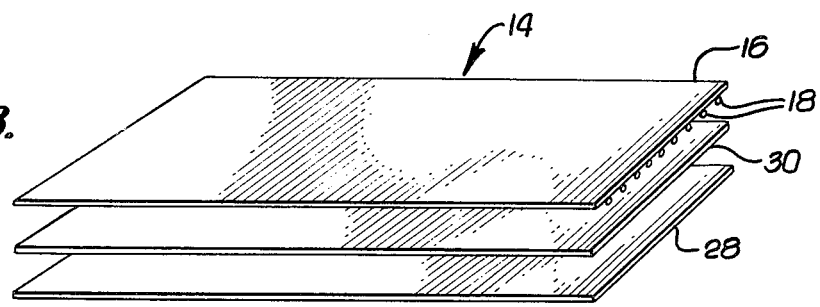
FIG. 3 is an exploded perspective view of the system embodying the invention, shown with an intensifying screen and film.

Referring now to the drawings, and particularly to FIG. 1 and FIG. 3, there is shown a new and improved diagnostic system exhibiting features of the present invention. The system utilizes immunoassays for coincident measurement of multiple allergens in liquid specimens.

In accordance with the present invention, a support 10 is combined with a plurality of threads 12 supported in a predetermined spaced relation for simultaneous contact with a liquid test sample. The system construction of the present invention is relatively easy to manufacture, and is flexible and inexpensive to use.

The support 10 may be made from a plastic or from other water insoluble materials that are easily cut and available in strips. The threads 12 are preferably made from cotton, a high molecular weight polysaccharide, to permit allergen binding through cyanogen halide induced linkages. At least two of the threads 12 are coated with allergen compositions for reaction with different IgE class antibodies.

Each thread 12 is activated with cyanogen bromide as follows. A standard cotton basting thread, such as Brooks D-96N, cotton covered polyester or mercerized cotton, all available from Coats & Clark, Inc., Atlanta, Ga., is wound onto a spindle, and about 3 grams placed in a beaker containing about 100 ml of fresh distilled water maintained at about 18° C. After adding a few drops of 1N NaOH to the water, 5 grams of cyanogen bromide in 100 ml distilled water are added, and the pH of the entire mixture monitored with a standard pH meter and the pH maintained at between about ten and eleven with 1N NaOH. After about one hour, the thread is placed in about one liter of 0.005M $NaHCO_3$, and the entire mixture is then poured over a sintered glass funnel. The thread held by the funnel, is washed five times with 250 ml of acetone and air dried for about one hour in a hood. The activated threads are stored with a dessicant in a petri dish covered with filter paper for two days or more at a temperature of about 4° C. prior to coupling.

A wide variety of allergens can be bound to the activated threads, and by way of example, the following list contains a few of the preferred. The list contains both the common and scientific names, along with the family for possible information on cross-reactivity.

Allergen

Birch (*Betula alba*) FAMILY: Alder
Cat (1:10 environment bulk cat hair, in 50% glycerol)
Cockleburr, spiny (*Xanthium spinosum*) FAMILY: Compositae
Curly dock (*Runnex crispus*) FAMILY: Polygoniaceae
English plantain (*Plantago lanceolata*) FAMILY: Plantaginaceae
False Ragweed (*Franseria acanthicarpa*) FAMILY: Compositae.
Grass Mix:
    a. Annual blue grass (*Poa annua*)
    b. Bermuda grass (*Cynodon dactylon*)
    c. English rye Grass (*Lolium perenne*)
    d. Fescue, tall meadow grass (*Festuca elatior*)
    e. Kentucky blue grass (*Poa pratensis*)
    f. Orchard grass (*Dactylis glomerata*)
    g. Redtop (*Agrostis alba*)

h. Salt grass (*Distichlis spicata*)
i. Sweet vernal grass (*Anthoxanthum odoratum*)
j. Timothy (*Phleum pratense*)

House dust (2,000pnu/ml Albay A.P., bulk in 50% glycerol)

Household insects

Juniper, western (*Juniperus occidentalis*)

Lambs quarter (*Chenopodiaceae album*) FAMILY: Chenopod

Live Oak (*Quercus agrifolia*)

Mite (1:100 mite bulk in 50% glycerin) *Dermatophagoides farinae*

Mugwort mix FAMILY: Compositae
  a. *Artemisia campestris pacifica*
  b. California (*Artemisia vulgaris heterophylla*)
  c. Coast sage (*Artemisia Californica*)
  d. Giant sagebrush (*Artemisia tridentata*)
  e. Sand sagebrush (*Artemisia filifolia*)
  f. Western sage (*Artemisia suksdorfii*)

Mustard (brassica) FAMILY: Cruciferaceae

Olive mix
  a. Ash, Oregana (*Fraxinus oregana*)
  b. Olive, (*Olea europia*)
  c. Privet (*Ligustrum vulgare*)

Pickleweed (*Salicornia ambigua*) FAMILY: Chenopodiaceae

Pigweed, Careless weed (*Amarantaceae palmeri*) FAMILY: Amarantacea

Ragweed: mix FAMILY: Compositae
  a. Short or common Ragweed (*Ambrosia elatior*)
  b. Western Ragweed (*Ambrosia psilostachla psilostachya*)

Russian thistle (*Salsola kali*) FAMILY: Chenopodiaceae

Sheep sorrel (*Rumex acetosella*) FAMILY: Polygonaceae

Spearscale (*Atriplex patula*) FAMILY: Chenopodiaceae

Walnut mix:
  a. California black (*Juglans californica*)
  b. English walnut (*Juglans regia*)

Aspergillus

Alternaria Mix
  a. Alternaria
  b. Helminthosporium
  c. Hormodendrum

Dematiaceae Mix

Dog hair and dander

*Monilia albicans*

Penicillium Mix

Many of the allergens may be purchased from Sharp & Sharp, Everett, Wash., or as extracts from Hollister Steir, Spokane, Wash. Alternatively, they may be isolated utilizing techniques well known in the art. Generally, if not available as an extract, the allergens must be defatted and extracted into a aqueous solution prior to final binding to the threads.

By way of example, for defatting and extracting pollen, 3 mls of diethylether are added to one gram of pollen powder. The preliminary extraction proceeds for about one hour, after which the ether is removed with an aspirator. This is repeated at least two times, and the defatted material allowed to dry overnight. About one gram of the defatted allergen is placed in 10 mls of 0.1M phosphate buffer, pH 7.5, containing 0.9 wt. % NaCl and 0.1 wt. % $NaN_3$. This solution is sonicated for about two minutes to properly suspend the allergen in the buffer, stored in a cold room for about 24 hours, and the sediment removed by centrifugation for about one hour. The supernatent is poured through a paper filter and a millipore filter of about 0.45 microns. If desired, the supernatent can be assayed for protein concentration by the well known Lowry method. Similarly, the amount of allergen present can be ascertained by standard radioimmunoassay techniques.

For coupling the allergens to activated threads, each allergen is first serially diluted in 0.1M $Na_2PO_4$ buffer, pH 7.5, with 0.9 wt. % NaCl and 0.1 wt. % $NaN_3$ (dilution buffer), to concentrations ranging from about 1 to 10 mg/ml. About 10 mg of activated threads are added to 1 ml of each dilution and gently rocked for about 24 hours at 4° C. The allergen dilution is then removed by aspiration and the threads washed two times with 0.1M $NaHCO_3$. Thereafter, the threads are mixed with 1 ml of 0.05M ethanolamine in 0.1M $NaHCO_3$. After incubating for about 3 hours, the ethanolamine is removed by aspiration and the threads washed repeatedly: two times each with 0.5M $NaHCO_3$; 0.1M $CH_3COONa$, pH 4.0; and the dilution buffer with 0.2% human serum albumin.

To determine an optimal bulk coupling concentration for the allergen, a sample test utilizing a pool of positive sera (i.e., sera containing IgE class antibodies reactive with the specific allergen band) is run with the dilutions. About a 2.5 cm length of a coated thread is added to a well with about 50 l of the pooled sera, and the well placed in a humid chamber containing $H_2O$ with 0.1 wt. % $NaN_3$. After incubating for about eighteen to twenty-four hours, the liquid is aspirated off and the thread washed five times with the dilution buffer.

The thread is then incubated in the chamber for about eighteen to twenty-four hours with a small volume, preferably about 50 l, of radioactively labeled second antibodies that are reactive with human IgE class antibodies. As is well known, suitable second antibodies can be obtained from the sera of goats or rabbits injected with human IgE, or from monoclonal sources, such as murine IgE available from Hybritech, Inc., La Jolla, Calif. The second antibodies are labeled with $I^{125}$ by traditional iodination techniques, such as described in Hunter and Greenwood, Nature 194: 495 (1962) and, if necessary, purified according to processes well known in the art.

After the incubation, the second antibody solution is aspirated off. The thread is again washed with five volumes of the dilution buffer, and then counted in a conventional gamma counter to quantify its radioactivity. The lowest serial dilution having a count level approximately equal to the maximum count level obtained from the serial dilutions is the optimal coupling concentration.

By way of example, the following list indicates a number of presently preferred coupling concentrations.

| ALLERGEN COUPLING CONCENTRATIONS | |
|---|---|
| Allergen | Concentration (mg/ml) |
| Birch | 2.0 |
| Cat | 0.05 |
| Cockleburr | 6.5 |
| Curly dock | 5.3 |
| English plantain | 2.0 |
| False Ragweed | 5.2 |
| Grass Mix | 0.05 |
| House dust | 3.0 |
| Household insects | 3.7 |

| ALLERGEN COUPLING CONCENTRATIONS | |
|---|---|
| Allergen | Concentration (mg/ml) |
| Juniper | 4.9 |
| Lambs quarter | 3.0 |
| Live oak | 0.5 |
| Mite | 0.1 |
| Mugwort mix | 1.0 |
| Mustard | 1.0 |
| Olive Mix | 0.1 |
| Pickleweed | 2.0 |
| Pigweed | 1.0 |
| Ragweed Mix | 5.4 |
| Russian thistle | 1.0 |
| Sheep sorrel | 4.0 |
| Spearscale | 1.0 |
| Walnut | 1.0 |
| Aspergillus | 4.5 |
| Alternaria mix | 2.6 |
| Dematiaceae mix | 3.9 |
| Dog hair and dander (IBI) | 2.7 |
| *Monilia albicans* | 2.6 |
| Penicillium mix | 3.0 |

Once the allergens have been coated onto the threads 12, the threads are placed in a predetermined spaced relationship, preferably parallel about 1.5 to 3.0 mm apart, along a support 10, such as a plastic having a heat sensitive coating. By utilizing a hot knife to cut the support along a cutting line, which is generally indicated by numeral 36, the threads 12 can bind to the support 10 as the heat sensitive coating melts. Thus, varying length strips with a number of threads, each coated with a different allergen, are readily prepared.

As shown in FIG. 3, a device 14 having a support 16 combined with the threads 18, all of which are coated with different allergens, is suitable for screening purposes. The device 14 is first placed in a liquid sample and incubated for a time sufficient to allow any IgE class antibodies present in the liquid sample to bind to the allergens on the threads. The device 14 is removed from the liquid sample, washed, and then incubated with a solution containing the previously described radioactively labeled second antibodies that are reactive with human IgE class antibodies. Thereafter, the device is removed from the radioactive second antibody solution, and the amount of radioactivity on the threads 18 determined.

Figure 6:
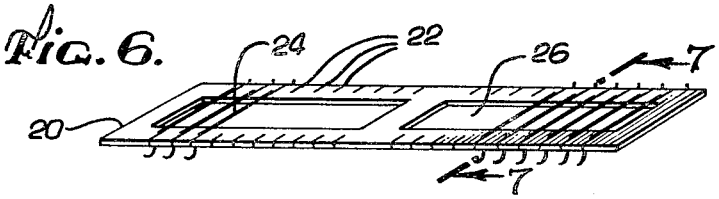
FIG. 6 is a perspective view of an alternative form of the system having a portion of the support cut away.
Figure 7:
FIG. 7 is a sectional view taken substantially along the line 7—7 in FIG. 6.

As illustrated in the alternative embodiment of FIG. 6 and FIG. 7, a support 20 may have a plurality of slits 22 aligned along opposite edges of the support to hold the threads 13 in a transverse fashion. Further, the support 20 may have interior portions cut away, indicated generally by the numeral 26, providing an open area behind the threads 24. This allows improved sensitivity due to the absence of a background. For example, when the support 20 is incubated in a radioactive second antibody solution, radioactivity could be absorbed and retained by the support even after repeated washings. By utilizing the cutaways 26 behind the threads 24, any radioactivity absorbed by the support 20 would not significantly interfere with subsequent analysis of the threads.

Figure 4:
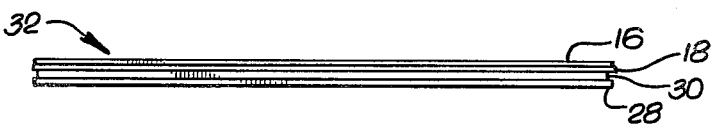
FIG. 4 is an end view of the system assembled with an intensifying screen and film.

In a preferred embodiment, the amount of radioactivity is determined autoradiographically. As illustrated in FIG. 3 and FIG. 4, the device 14 is placed proximate to a standard X-ray film 28, such as Kodak, Ortho H X-ray film, with the threads 18 facing the film. To promote exposure, a radio-absortive, photon emitting phosphorous screen 30, such as EK Lanex available from the Picker Corporation, or described in "X-Ray Exposure Reduction Using Rare-Earth Oxysulfide Intensifying Screens", Buchanan et al, Radiology 105: 185-90 (1972), is then placed between the device 14 and film 28. Alternatively, two phosphor screens may sandwich the film 28 and device 14 (not shown). The assembly 32 is held in a dark room for a period of time sufficent to expose the film to any radioactivity on the threads, and then developed. When the radioactivity on a thread exceeds 20,000 cpm, an exposure time of one hour is acceptable. Similarly, for 5,000-20,000 cpm, an exposure time of eight hours is preferred, and for 1,000-5,000 cpm, 21 hours can be utilized. The length of exposure time will, of course, vary with the type of film, phosphor screen and other parameters.

Figure 5:
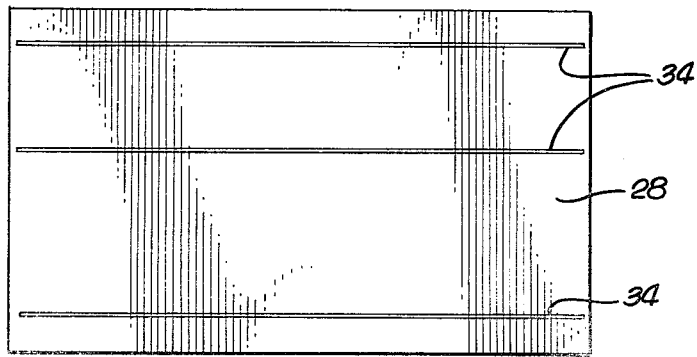
FIG. 5 is a top plan view of the film partially exposed.

FIG. 5 illustrates the film 28 having three exposure lines 34 from the exposure during positioning in the assembly 32. The lines 34 indicate that the liquid specimen contained IgE class antibodies specific for the allergen coated on each complementary thread 18.

From the foregoing, it will be appreciated that the diagnostic system of the present invention allows the coincident determination of a large number of allergens in a liquid specimen, thereby providing an effective allergy screening system. Further, the system is very economical, in that it is simple to manufacture and, additionally, is easy and inexpensive to analyze.

While a particular form of this invention has been illustrated and described, it will be apparent that various modifications may be made without departing from the spirit and scope of the invention.

I claim:

1. For use in the diagnostic analysis of a liquid specimen through binding assays, a diagnostic system comprising a plurality of filaments supported in a spaced relationship for simultaneous contact with said liquid specimen, at least two of said filaments being coated with binding assay components from different assays, for multiple, coincident measurement of said assays.

2. The diagnostic system of claim 1 wherein said binding assay component is an antigen.

3. The diagnostic system of claim 1 wherein said binding assay component is an allergen.

4. The diagnostic system of claim 1 wherein said filaments consist essentially of cotton.

5. The diagnostic system of claim 1 wherein said filaments are threads.

6. A diagnostic test kit useful in screening for the presence of multiple allergen-specific IgE class antibodies in a liquid test sample, said kit comprising a plurality of threads supported in a predetermined spaced relationship for simultaneous contact with said test sample, wherein at least two of said threads are coated with allergen compositions specific to different IgE class antibodies.

7. The kit of claim 6 wherein the threads are cotton.

8. The kit of claim 6 wherein the threads consist essentially of a polysaccharide.

9. The kit of claim 6 wherein each allergen composition is bound to a thread through a covalent bond.

10. The kit of claim 9 wherein said covalent bond is formed with a cyanogen halide.

11. The kit of claim 6 further comprising labeled antibodies reactive with said IgE for detection and measurement of IgE class antibodies bound to said thread.

12. The kit of claim 11 wherein the antibodies reactive with said IgE class antibodies are labeled with a radioactive tracer.

13. The kit of claim 12 wherein said radioactive tracer is $^{125}$I.

14. The kit of claim 11 wherein the antibodies reactive with said IgE class antibodies are labelled with a fluorescent tracer.

15. The kit of claim 11 wherein the antibodies reactive with said IgE class antibodies are labelled with an enzyme.

16. The kit of claim 11 wherein the antibodies reactive with said IgE class antibodies are labeled with an enzyme substrate or coenzyme.

17. A method of detecting the presence of biological agents in a liquid specimen through binding assays, said method comprising the steps of: incubating said liquid specimen with a plurality of filaments supported in a predetermined spaced relationship, at least two of said filaments being coated with binding assay components from different assays; and analyzing said filaments to coincidently determine which of the biological agents, interact with said binding assay component coated on each of said filaments.

18. The method of claim 17 wherein said binding assays are immunoassays.

19. The method of claim 17 wherein said binding assay components are allergens.

20. The method of claim 17 wherein said filaments are analyzed by autoradiography.

21. A method of screening for the presence of multiple allergen-specific IgE class antibodies in a liquid test sample, said method comprising the steps of: incubating said test sample with a plurality of filaments supported on a support in a predetermined spaced relationship and coated with allergens specific to said IgE class antibodies; removing said filaments from said test sample; incubating said filaments with a solution containing labeled antibodies that are reactive with said IgE class antibodies; removing said filaments from said solution; and analyzing said filaments to determine the presence of said labeled antibodies; wherein at least two of said filaments are coated with different allergens.

22. The method of claim 21 wherein the labeled antibodies are radioactive.

23. The method of claim 22 wherein the radioactive antibodies contain $^{125}$I.

24. The method of claim 22 wherein the analysis is accomplished with a gamma counter.

25. The method of claim 22 wherein the analysis of the filament for the presence of labeled antibodies is accomplished by placing the filaments proximate to a film for exposing said film by said labeled antibodies.

26. The method of claim 25 wherein one or more phosphor screens are placed adjacent said film and said filaments to increase film exposure.

27. The method of claim 25 wherein the film is read by the unaided human eye.

28. The method of claim 25 wherein the film is read by a densitometer.

29. The method of claim 28 wherein the densitometer is a scanning densitometer.

30. The method of claim 21 wherein the labeled antibodies are fluorescent.

31. The method of claim 30 wherein the analysis of the filaments for the presence of labeled antibodies is accomplished with a fluorometer.

32. The method of claim 21 wherein the labelled antibodies are labeled with an enzyme, enzyme substrate or coenzyme.

33. The method of claim 21 wherein the analysis is accomplished with a spectrophotometer.

34. The method of claim 21 wherein a portion of the support is cut away to minimize background interference.

35. The method of claim 21 wherein the plurality of filaments comprises at least about eight filaments.

36. A method of making an apparatus useful in the diagnostic analysis of liquid specimens through binding assays, said method comprising the steps of: coating each of a plurality of filaments with components of different binding assays; and attaching the coated filaments to a support such that they are arranged in spaced relationship.

37. The method of claim 36 wherein said binding assay is an immunoassay.

38. The method of claim 36 wherein said binding assay component is an antigen.

39. The method of claim 36 wherein said binding assay component is an allergen.

40. The method of claim 36 wherein said support consists essentially of water insoluble material.

41. The method of claim 36 further comprising the step of cutting the support and attached filaments into a plurality of elongated strips of predetermined size.

42. The method of claim 36 wherein said binding assay component is covalently bound to said filament.

43. The method of claim 36 wherein said filament is a cotton thread.

44. A method of making a miniature apparatus for use in the simultaneous determination of the presence of multiple allergen-specific IgE class antibodies in a liquid test sample, said method comprising the steps of: coating a filament with an allergen composition specific to at least one of said IgE class antibodies; and attaching a plurality of said filaments to a support; wherein at least two of said filaments attached to said support are coated with different allergen compositions.

45. The method of claim 44 further comprising the step of cutting said support and attached filaments into a plurality of elongated strips of predetermined size.

46. The method of claim 44 wherein one of said allergen composition comprises a mixture of related allergens.

47. The method of claim 46 wherein said mixture is a grass mix, mugwort mix, olive mix, ragweed mix, walnut mix, alternaria mix, dematiaceae mix or penicillium mix.

48. The method of claim 44 wherein said allergen composition is a defatted and extracted allergen.

49. The method of claim 48 wherein said allergen composition is covalently bound to said filament.

50. The method of claim 49 wherein said filament is a cotton thread.

51. The method of claim 50 wherein said covalent bond is formed with cyanogen bromide.

52. The diagnostic system of claim 1 wherein:
the system further includes an elongated, flat support on which the plurality of filaments are supported; and
the filaments are oriented substantially parallel to each other and perpendicular to the longitudinal axis of the support.

53. The diagnostic system of claim 52 wherein the support contacts the filaments only at their respective ends.

54. A method of detecting the presence of multiple biological agents in a liquid specimen through binding assays, comprising steps of:
incubating the liquid specimen with a diagnostic device having a plurality of filaments secured to a support member, at least two of the filaments being coated with binding assay components that react with different biological agents that might be present in the specimen;
separating the liquid specimen and the diagnostic device from each other;
incubating the diagnostic device with a solution containing labeled components that will bind to any of the biological agents that might have bound to the binding assay components in the first step of incubating;
separating the diagnostic device and the solution from each other; and
positioning the diagnostic device proximate to a photographic film, to expose a pattern in the film indicative of the presence of labeled components on each of the filaments.

55. The method of claim 54 wherein:
the labeled components present in the solution used in the second step of incubating are labeled with a radioactive tracer; and
the method further includes a step of positioning a phosphor screen adjacent to the photographic film, to enhance the film exposure.

56. The method of claim 54 wherein:
the filaments are secured at least at their opposite ends to the support member in a substantially parallel and spaced apart relationship such that the step of positioning results in a pattern of spaced lines being exposed in the film, each such line having an exposure indicative of the concentration of labeled components on the corresponding filament; and
the method further includes a step of measuring the exposure of the spaced lines in the film.

57. The method of claim 54 wherein:
the biological agents detected by the method are allergen-specific IgE class antibodies;
the binding assay components coated on the filaments are allergens; and
the labeled components contained in the solution used in the second step of incubating are anti-IgE antibodies.

* * * * *